United States Patent
Walker, Jr.

(10) Patent No.: US 7,346,205 B2
(45) Date of Patent: Mar. 18, 2008

(54) SYSTEM AND METHOD FOR RAPIDLY IDENTIFYING PATHOGENS, BACTERIA AND ABNORMAL CELLS

(75) Inventor: Fitz Walker, Jr., New Haven, CT (US)

(73) Assignee: Bartron Medical Imaging, LLC, New Haven, CT (US)

( * ) Notice: Subject to any disclaimer, the term of this patent is extended or adjusted under 35 U.S.C. 154(b) by 290 days.

(21) Appl. No.: 10/550,076

(22) PCT Filed: Mar. 25, 2004

(86) PCT No.: PCT/US2004/009172

§ 371 (c)(1),
(2), (4) Date: Sep. 20, 2005

(87) PCT Pub. No.: WO2004/086941

PCT Pub. Date: Oct. 14, 2004

(65) Prior Publication Data

US 2007/0054350 A1    Mar. 8, 2007

Related U.S. Application Data

(60) Provisional application No. 60/458,769, filed on Mar. 27, 2003, provisional application No. 60/505,944, filed on Sep. 25, 2003.

(51) Int. Cl.
  *G06K 9/00* (2006.01)

(52) U.S. Cl. ..................................... 382/133; 382/173
(58) Field of Classification Search ................ 382/128, 382/132, 133, 134, 173, 180, 217, 218, 226, 382/227, 302, 304
See application file for complete search history.

(56) References Cited

U.S. PATENT DOCUMENTS

| | | | | |
|---|---|---|---|---|
| 5,742,700 | A | * | 4/1998 | Yoon et al. ................. 382/132 |
| 5,995,668 | A | * | 11/1999 | Corset et al. ............... 382/233 |
| 6,895,115 | B2 | | 5/2005 | Tilton ........................ 382/180 |
| 2002/0165837 | A1 | | 11/2002 | Zhang et al. ................. 706/16 |
| 2003/0026493 | A1 | * | 2/2003 | Kamath et al. ............. 382/260 |
| 2006/0257053 | A1 | * | 11/2006 | Bourdreau et al. ......... 382/305 |

\* cited by examiner

*Primary Examiner*—Andrew W. Johns
(74) *Attorney, Agent, or Firm*—Raymond Nuzzo

(57) ABSTRACT

The present invention achieves rapid identification of pathogens, bacteria, cancer cells and other abnormal human and animal cells. In one embodiment, the system of the present invention comprises a first subsystem that obtains and processes images of specimens of pathogens, bacteria, and other abnormal cells, and a second subsystem that accepts the images, isolates the particular features of the image using advanced image segmentation, and then rapidly and accurately identifies the pathogens, bacteria and other abnormal cells by using a pattern recognition process wherein the segmented or isolated features of the original image are compared to known reference images.

12 Claims, 10 Drawing Sheets

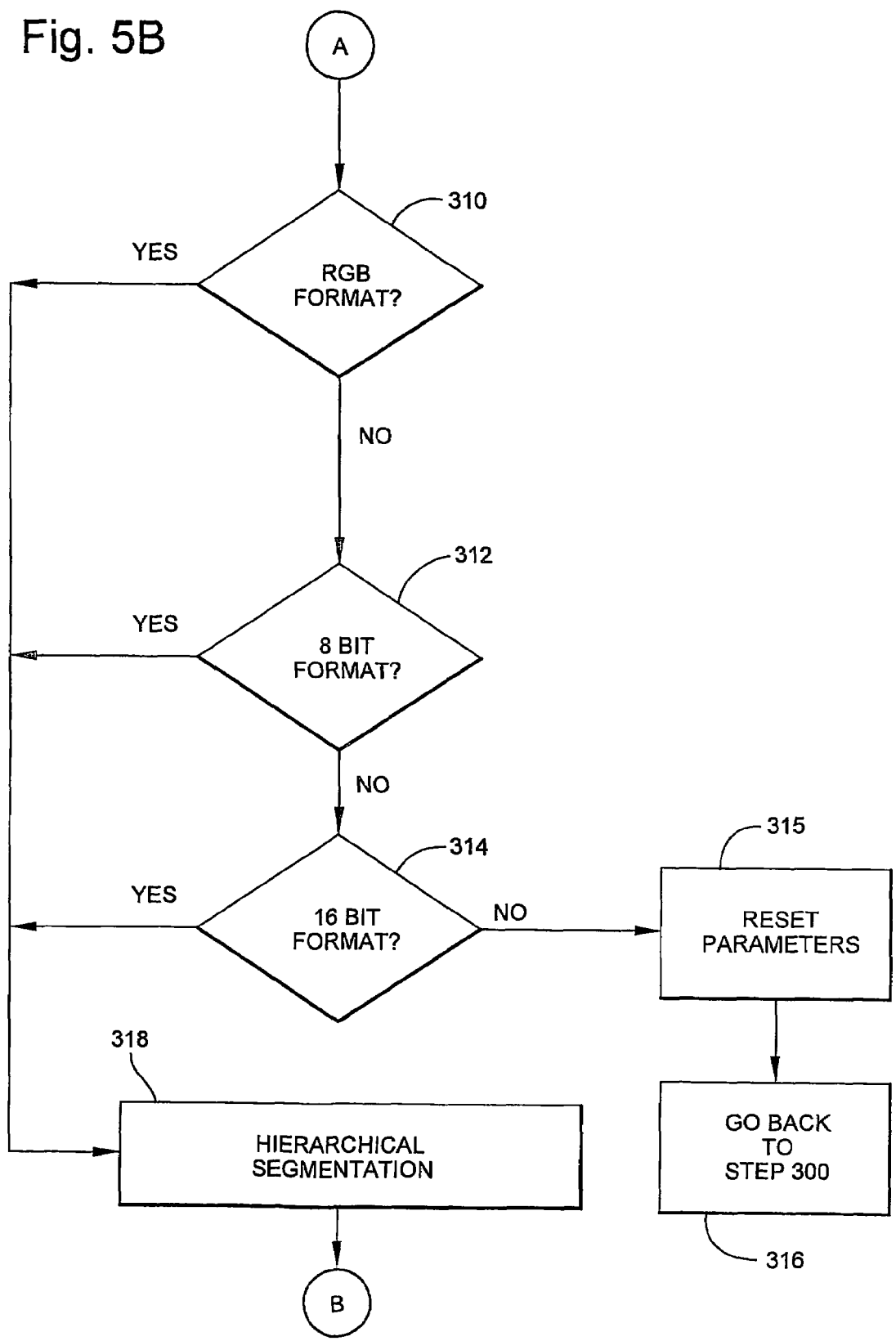

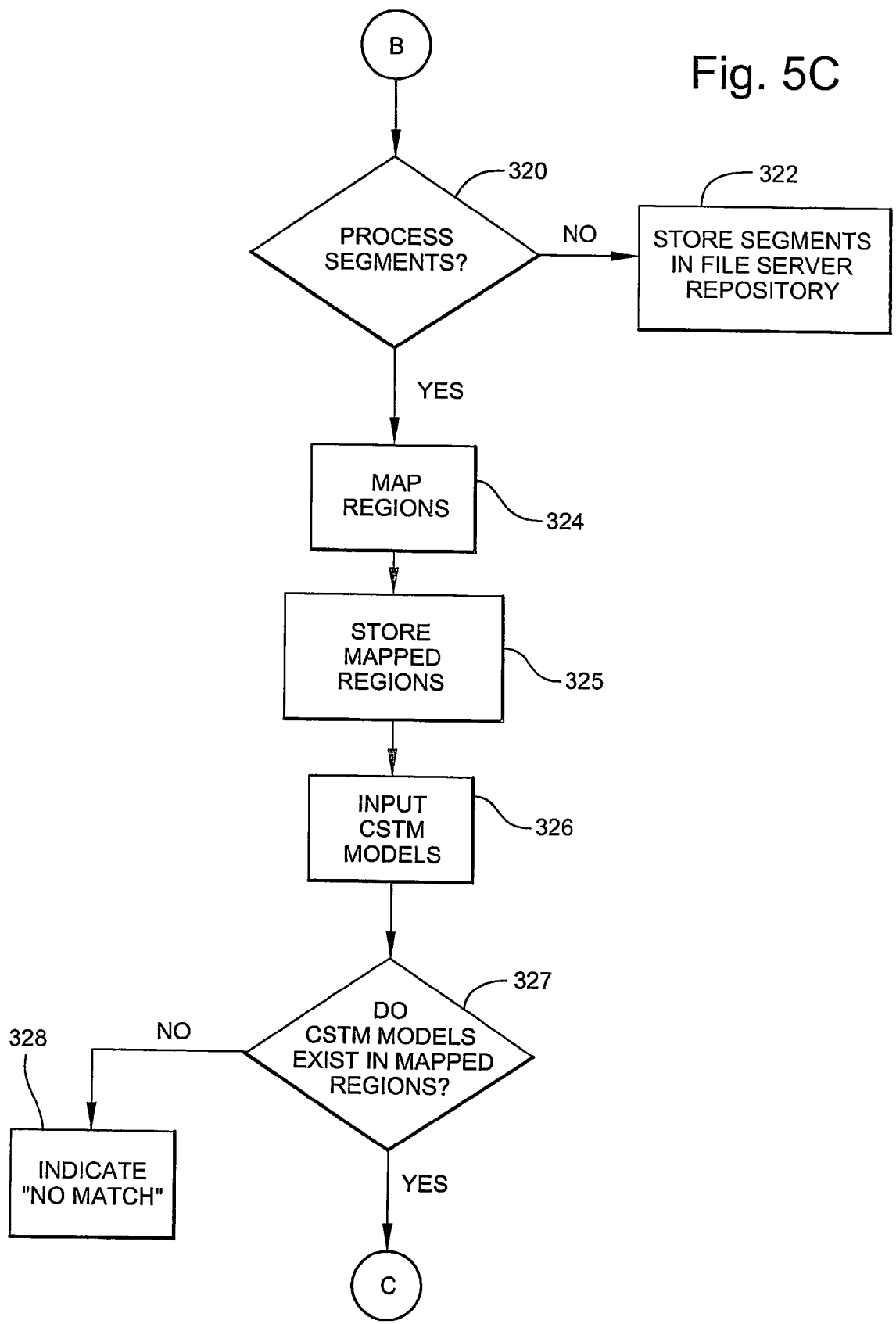

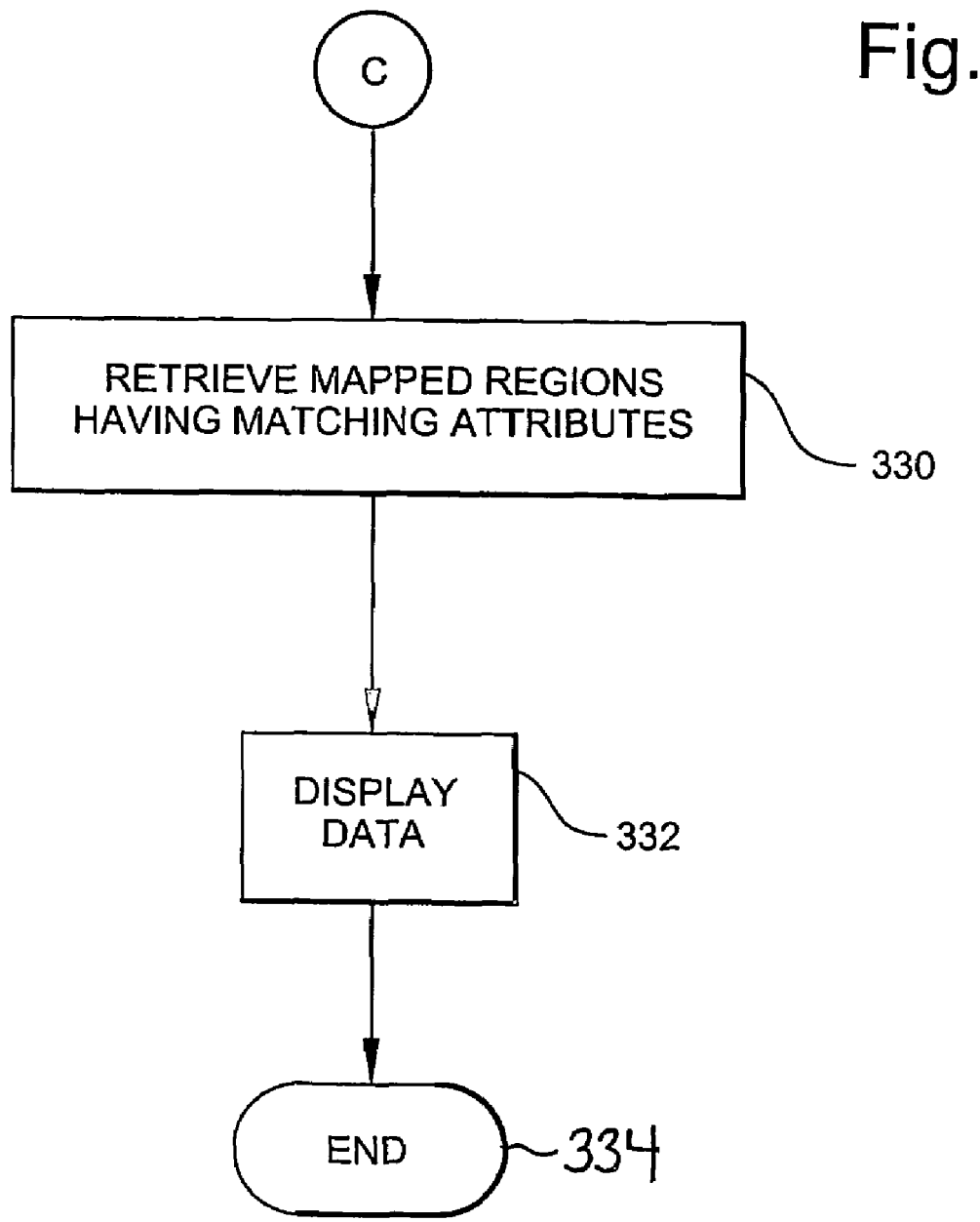

SYSTEM AND METHOD FOR RAPIDLY IDENTIFYING PATHOGENS, BACTERIA AND ABNORMAL CELLS

CROSS-REFERENCE TO RELATED APPLICATIONS

This application is the national stage of International Application PCT/US04/09172, filed Mar. 25, 2004, which claims the benefit of commonly owned and copending U.S. Provisional Application Ser. Nos. 60/458,769, filed Mar. 27, 2003, and 60/505,944, filed Sep. 25, 2003.

TECHNICAL FIELD

The present invention generally relates to a system and method for identifying pathogens and abnormal cells.

BACKGROUND ART

The timely diagnosis of pathogens, bacteria, abnormal cell and infectious diseases is often complicated by the need to use cultures as the means to identify the bacteria and select the optimum treatment. Currently, identification of pathogens often takes days and involves complicated procedures, a situation that may unduly delay effective treatment such as the appropriate selection of an optimal antibiotic. Similar problems exist in detecting bacterial contamination in food, especially in beef, poultry and fish. The delay in identifying the presence of harmful bacteria in food products could result in contaminated products being released for distribution and consumption with dire consequences. In some instances, these delays have proved to be fatal to patients or have caused unnecessary suffering. According to 1999 statistics provided by the Center for Disease Control, there were 1,194,959 reported cases of infectious diseases caused by bacteria. Furthermore, there were many instances of food poisoning that were not subject to mandatory reporting to the Center for Disease Control. A common practice in treating infected patients is the use of broad-spectrum antibiotics. However, due to the problem of bacterial resistance to many antibiotics, broad-spectrum antibiotics may not be effective. Many of these cases of infectious diseases could have been prevented or promptly treated if rapid and accurate diagnosis was available. Rapid identification of pathogens, bacteria and abnormal cells is also critical in dealing with bio-terrorism and with biological agents during warfare.

DISCLOSURE OF THE INVENTION

The present invention achieves rapid identification of pathogens, bacteria and other abnormal human and animal cells. In one embodiment, the present invention is directed to a non-invasive system and method for automatically and rapidly identifying pathogens. In accordance with one embodiment of the invention, the system comprises a first subsystem that obtains and processes images of specimens of pathogens, bacteria or other abnormal cells, and a second subsystem that accepts the images of the specimens, isolates the particular features of each image using advanced image segmentation, and then rapidly and accurately identifies the pathogens, bacteria or abnormal cell structure using pattern recognition processing on the particular isolated features.

In one embodiment, the first subsystem described in the foregoing description comprises an image capturing system that comprises a microscope and a video camera. The image capturing system captures or acquires an image of a specimen of a pathogen, bacteria or abnormal cell structure, and then enhances, digitizes and temporarily stores the pertinent parts of the captured or acquired image of the specimen. The first subsystem further comprises a communication system that transmits the processed image to the second subsystem via any one of a variety of suitable communication schemes such as satellite links, the Internet, or telephone lines. In a preferred embodiment, the first subsystem further includes a computer, microprocessor or other controller to control the operation of the first subsystem. In a preferred embodiment, the first subsystem is configured to have automatic operation so as to minimize the manual effort in processing the image of the specimens.

In one embodiment, the second subsystem is typically located at a central location. The second subsystem receives the processed image transmitted by the first subsystem. The second subsystem comprises an image processing system that processes the images received from the first subsystem so as to isolate certain features of the image of the specimens that are of interest. This image processor effects image segmentation to isolate the aforementioned features of the image. The second subsystem comprises a database that contains known reference images. Such a data base functions as a library of images of known pathogen cells, bacteria cells and abnormal cells. Each reference image is associated with a known pathogen, bacteria or abnormal cell structure. The image processing system implements a data mining program that extracts particular image data from the isolated features and a pattern recognition program that compares the extracted image data to the known reference images in the database in order to determine if the isolated feature corresponds to or matches any of the known reference images.

The system and method of the present invention can also be used as a diagnostic radiology and imaging tool in the medical and dental field. Specifically, the system and method of the present invention can be configured to analyze medical images such as images of soft tissue, mammograms, x-rays (bone and dental), ultrasounds, MRI images, and CAT scans.

In another embodiment, the system is configured so that the first subsystem and second subsystem are joined together to form one main system that is located at one location. Such a configuration would be suitable for a large city hospital or one of the many teaching hospitals in the United States and throughout the world.

Thus, the present invention is directed to, in one aspect, a method for identifying pathogens, comprising providing an image, processing the provided image with an image segmentation algorithm to isolate at least one segment of the provided image that has a feature that is of interest, and comparing the isolated segment of the provided image to a plurality of reference images to determine if the isolated segment corresponds to any of the reference images.

In a related aspect, the present invention is directed to a system for identifying pathogens, comprising a device to provide an image, a data base having at least one reference image stored therein, and an image processing resource to (i) process the provided image with an image segmentation algorithm to isolate at least one segment of the provided image that has a feature of interest, and (ii) to compare the isolated segment of the provided image to the reference image to determine if the isolated segment corresponds to the reference image.

BRIEF DESCRIPTION OF THE DRAWINGS

The features of the invention are believed to be novel. The figures are for illustration purposes only and are not drawn to scale. The invention itself, however, both as to organization and method of operation, may best be understood by reference to the detailed description which follows taken in conjunction with the accompanying drawings in which:

FIGS. 5A-5D show a flow chart illustrating the operation of the image management diagnostic subsystem shown in FIG. 5.

MODES FOR CARRYING OUT THE INVENTION

Figure 1:
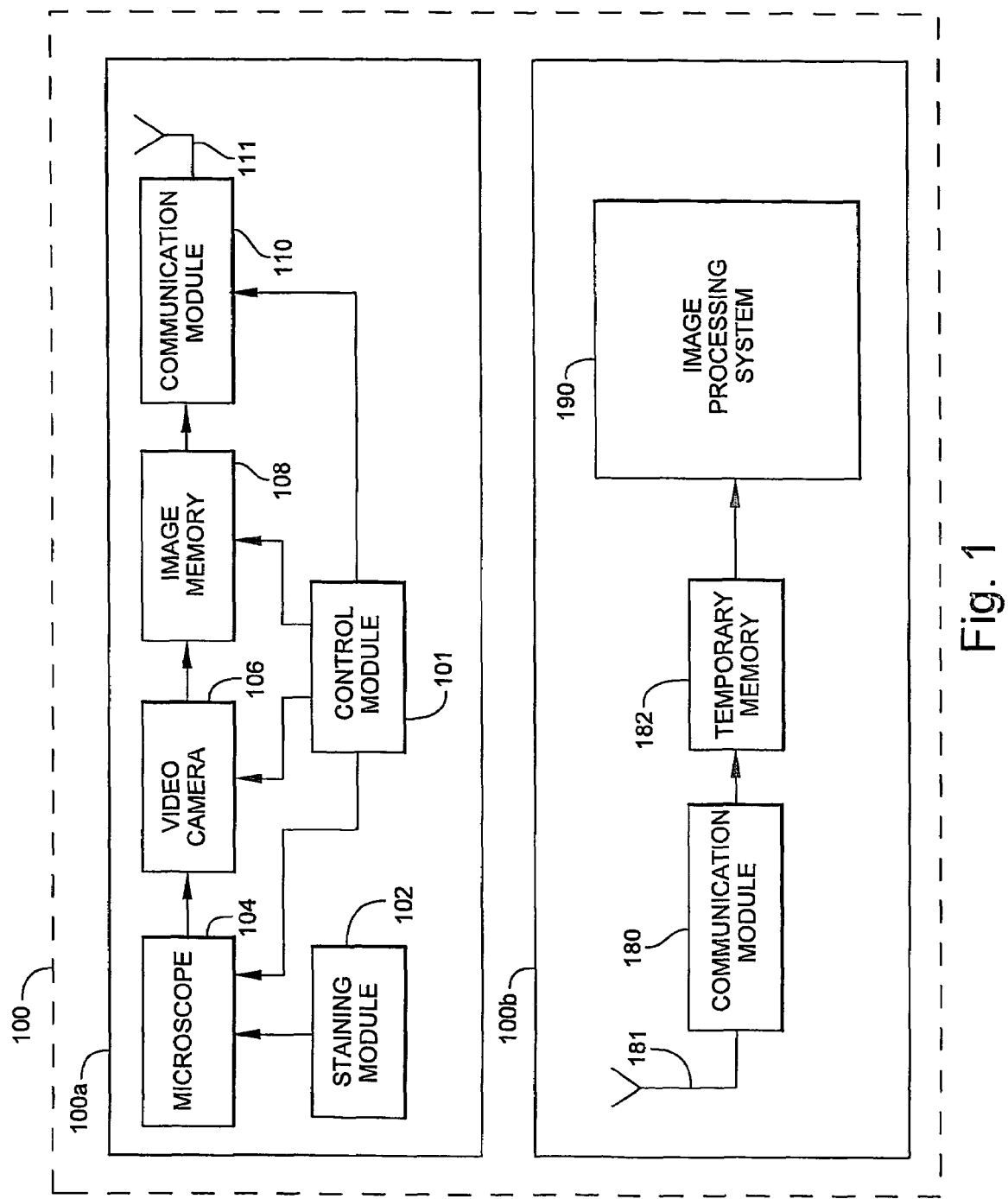
FIG. 1 is a block diagram of the system of the present invention.

Referring to FIG. 1, there is shown a block diagram of a system for rapid identification of pathogens, bacteria and abnormal cell structures in accordance with the invention. System 100 generally comprises imaging subsystem 100a and image management diagnostic subsystem 100b. Subsystem 100a generally comprises computer or controller 101, staining module 102, microscope 104, digital color video camera 106, image memory 108 and communications module 110. As will be apparent from the ensuing description, computer 101 controls the operation and the sequence of operation of microscope 104, digital color video camera 106, image memory 108 and communications system 110.

Referring to FIG. 1, staining module 102 stains the slides of specimens of pathogens, bacteria and abnormal cells that are affixed to slides. The slides are stained prior to being viewed with microscope 104. In a preferred embodiment, staining module 102 is a commercially available immune staining procedures module. One such suitable commercially available immune staining procedures module is known in the art as motorized furescence filters for accurate color imaging of the stained cells. In a preferred embodiment, between five and ten different stains are selected to stain a predetermined number of slides for a given specimen in order to ensure that at least one of these slides has a pathogen, bacteria or abnormal cell stained to produce an acceptable image.

In one embodiment, statistical analysis is used to determine a sufficient number of specimen slides that are needed to ensure that at least one of the slides contains the offending pathogen, bacteria, etc. Staining module 102 is configured to utilize a standard set of stains to cover the range of pathogens, bacteria, etc. of interest.

Referring to FIG. 1, microscope 104 is configured to provide sufficient magnification and includes an oil immersion objective, an optical port for video camera 106, an auto stage mechanism, and an auto focus mechanism. The auto stage mechanism comprises a shallow well for the convenient placement of the specimen slides. The automatic stage mechanism performs a raster scan of each slide while the auto focus mechanism maintains the image in focus. The auto stage mechanism is configured to stop briefly at each step to allow an image to be acquired. Each acquired image is assigned the x-y coordinates of the position of the auto stage mechanism. These x-y coordinates are automatically added in an appropriate format to the acquired image of the specimen.

Referring to FIG. 1, video camera 106 is controlled by computer or controller 101 to capture or acquire a color image of the specimen at each stop of the auto stage mechanism of microscope 104. Video camera 106 is configured to provide adequate resolution and stability. Video camera 106 digitizes the acquired image. The digitized image is then transferred to image memory 108. Image memory 108 is a temporary memory having sufficient data storage capacity to temporarily store the acquired images generated by video camera 106.

In a preferred embodiment, microscope 104 and video camera 106 are realized as a single, commercially available compact unit which combines the functions of both microscope 104 and video camera 106. One such commercially available unit is the Leica Model DMRXA2 Microscope. Other suitable, commercially available devices that combine a microscope and video camera into a single unit may be used as well.

In an alternate embodiment, the acquired images are pre-screened and presorted for useful and relevant content. This is accomplished by a screening processor and display device (both of which not being shown) that is in electronic data communication with image memory 108. This pre-screening and presorting function ensures that further analysis is performed only on images having relevant information. The screening processor utilizes predetermined criteria (descriptors) to determine whether the images have relevant content.

Referring to FIG. 1, computer 101 controls image memory 108 to transfer stored digitized images into communications module 110. In one embodiment, communications module 110 includes RF (radio frequency) antenna 111. However, communications module 110 is preferably configured to transmit the digitized images to second subsystem 100b via any one of a variety of suitable communications modes, e.g. telephone lines, the Internet, dedicated lines or RF communication or communication through satellite communication. In accordance with the invention, the communications link between first subsystem 100a and second subsystem 100b is bi-directional. In a preferred embodiment, the communication between first subsystem 100a and second subsystem 10b is real time. In one embodiment, communications module 110 is realized as a DSL Speedstream Model 5260.

In a preferred embodiment, a suitable, commercially available PC (personal computer) high end system is used to realize control module 101 and image memory 108.

In an alternate embodiment, subsystem 100a can be realized by separate, suitable commercially available components. For example, microscope 104 can be realized by a suitable, commercially available electronic or digital microscope. Similarly, video camera 106 can be realized by a suitable video camera that can provide a color image based on the image provided by the digital microscope.

Figure 2:
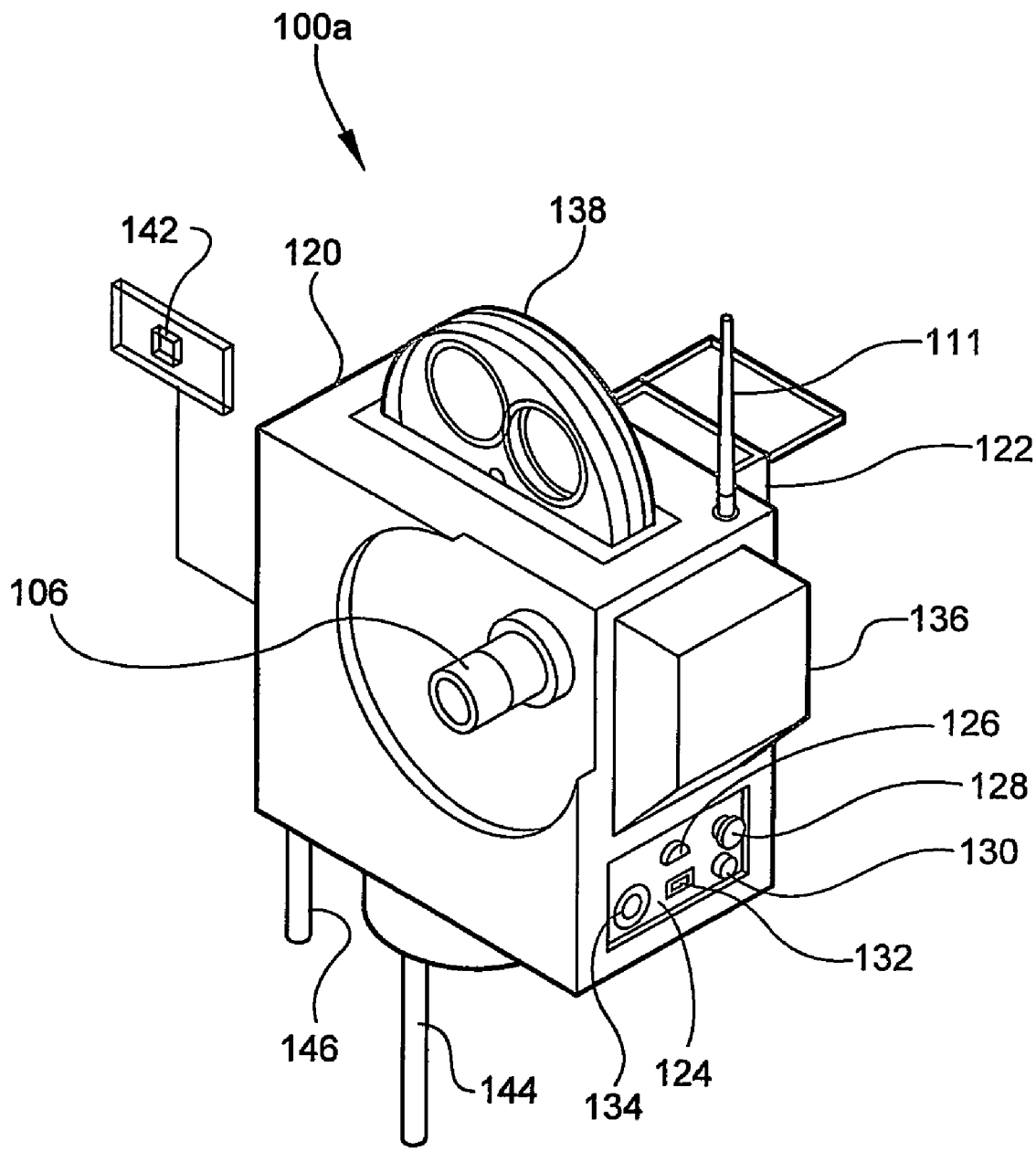
FIG. 2 is a perspective view of one embodiment of an imaging subsystem shown in FIG. 1.
Figure 3:
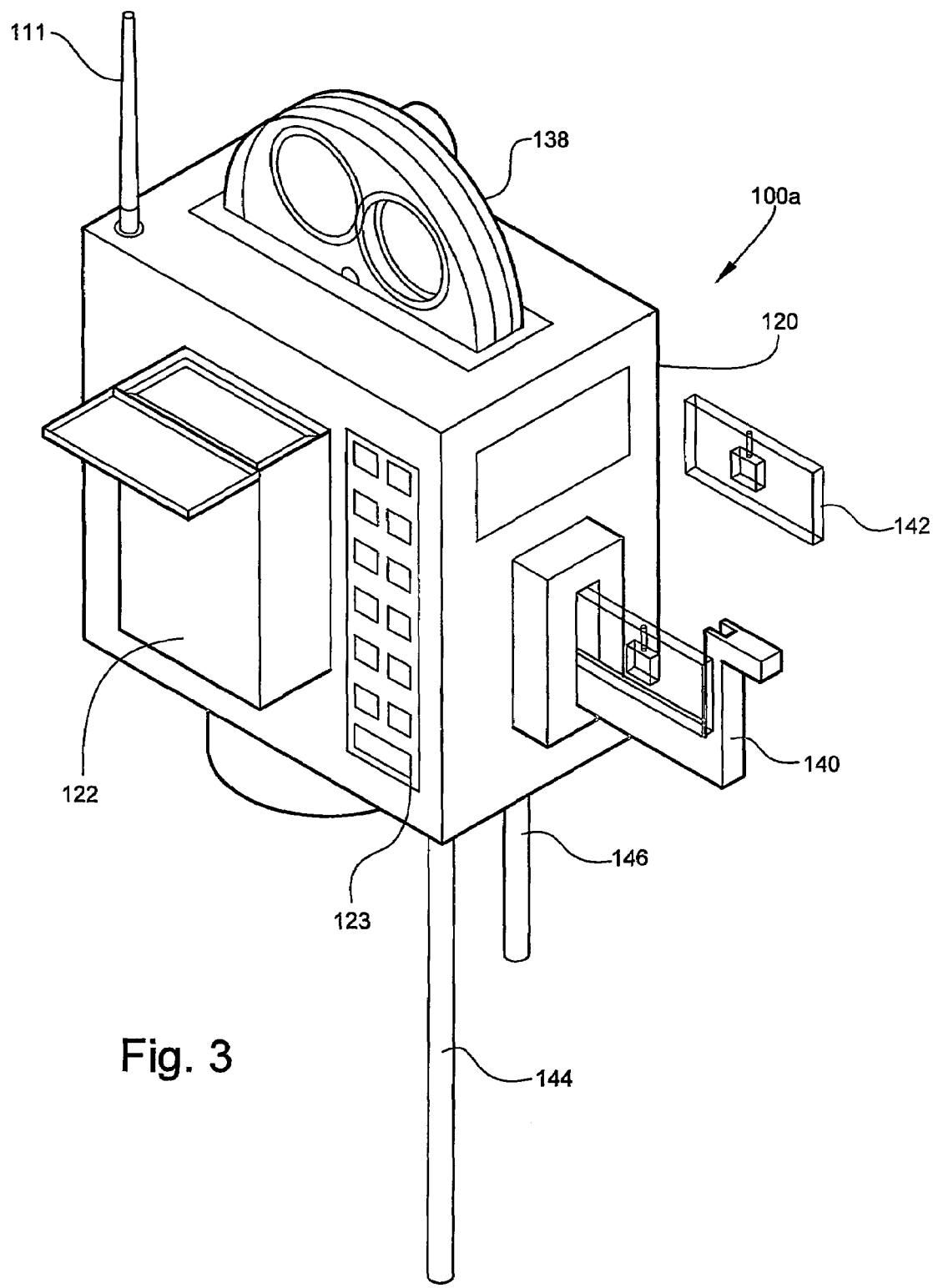
FIG. 3 is a perspective view of the rear side of the imaging subsystem of FIG. 2.

Referring to FIGS. 2 and 3, there is shown imaging subsystem 100a in accordance with an alternate embodiment of the invention. In this embodiment, all the components of subsystem 100a are combined into a single unit that is portable, compact, robust, and capable of battery-power operation or AC power to allow for mobile operation or operation in remote locations. This embodiment of image subsystem 100a has housing 120, control panels 122 and 123, and interface 124. Interface 124 comprises RS 232 interface 126, video data ports 128 and 130, USB port 132 and external power input 134. Rechargeable battery pack 136 supplies power to all other components. Screen 138 allows capture of air samples that are to be analyzed thereby allowing airborne pathogens, bacteria, etc. to be analyzed. Slide insertion device 140 enables a user to insert a specimen slide 142 into housing 120. Fluid inlet 144 and fluid outlet 146 allow for the ingress and egress of fluids (e.g. water) that is to be analyzed. In an alternate embodiment, the particular embodiment of subsystem 100a shown in FIGS. 2 and 3 is configured to operate with power from a land vehicle's battery.

Figure 4:
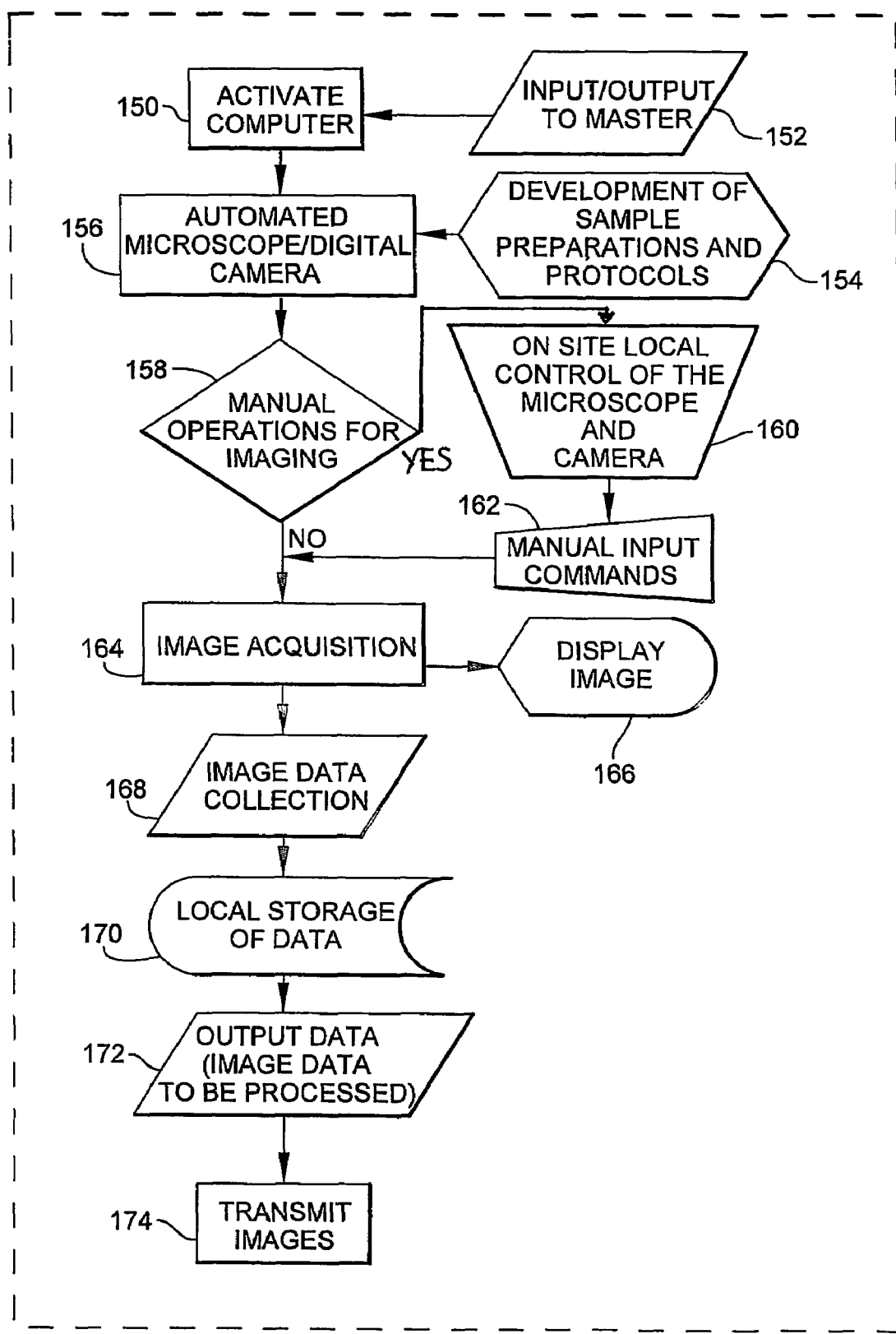
FIG. 4 is a flow chart illustrating the operation of the imaging subsystem shown in FIG. 1.

Referring to FIGS. 1 and 4, there is shown a flow chart illustrating the operation of imaging subsystem 100a. In step 150, a user activates computer 101. In step 152, any required data stored in a master system (not shown) is loaded into computer 101. In step 154, there occurs the development of the sample or specimen, preparations and protocols. In this step, the specimen is stained by staining module 102. In step 156, microscope 104 and video camera 106 are activated by computer 101, and a stained specimen slide is provided to microscope 104. Next, in steps 158, 160 and 162, it is determined whether the imaging of the specimen slides is going to be controlled manually (i.e. locally). If it is decided that there will be manual control, the user inputs manual input commands into computer 101 in order to control microscope 104 and video camera 106 according to the data defined by such commands. Next, in step 164, an image of the specimen is produced. In step 166, the produced image of the specimen is displayed on an external display device (not shown) such as computer screen or LCD which may be connected to either computer 101 or video camera 106. Included in steps 164 and 166 are the steps of pre-screening and pre-sorting of the images in order to determine if the image contains relevant information. In one embodiment, medical personnel pre-screen the images by visual inspection. In step 168, the relevant images are collected and organized in image memory 108. In step 170, the relevant images are stored in image memory 108 or in an external data storage device (not shown) such as a ROM or CD-ROM. In one embodiment, the external data storage device is an external device that is in electronic data communication with image memory 108. In step 172, the relevant collected and organized images are sent to an output buffer memory and then, routed to communications module 110. In step 174, these images are then communicated to image management diagnostic subsystem 100b with communication module 110.

Figure 5:
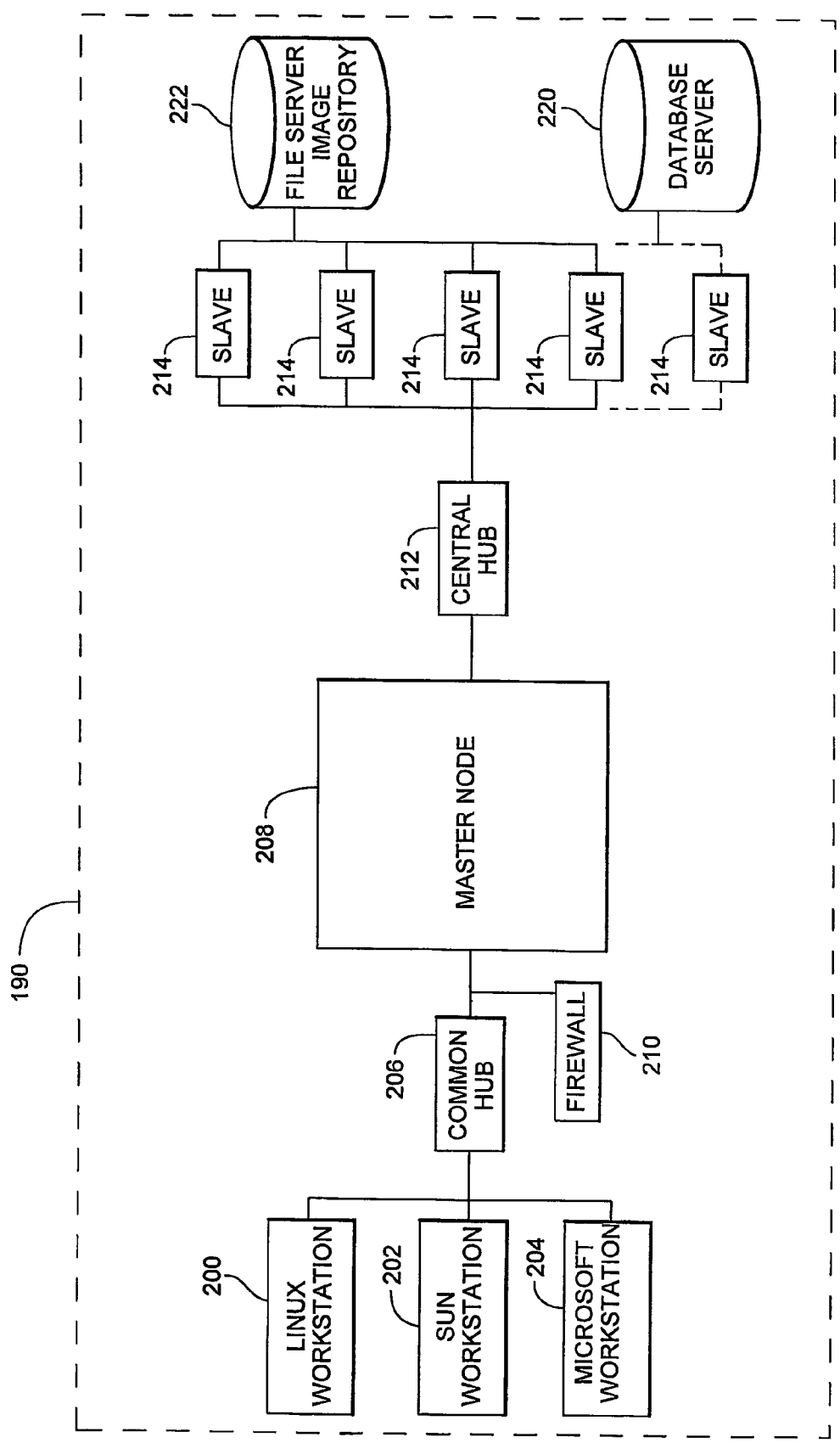
FIG. 5 is a block diagram of an image management diagnostic subsystem shown in FIG. 1.
Figure 5A:
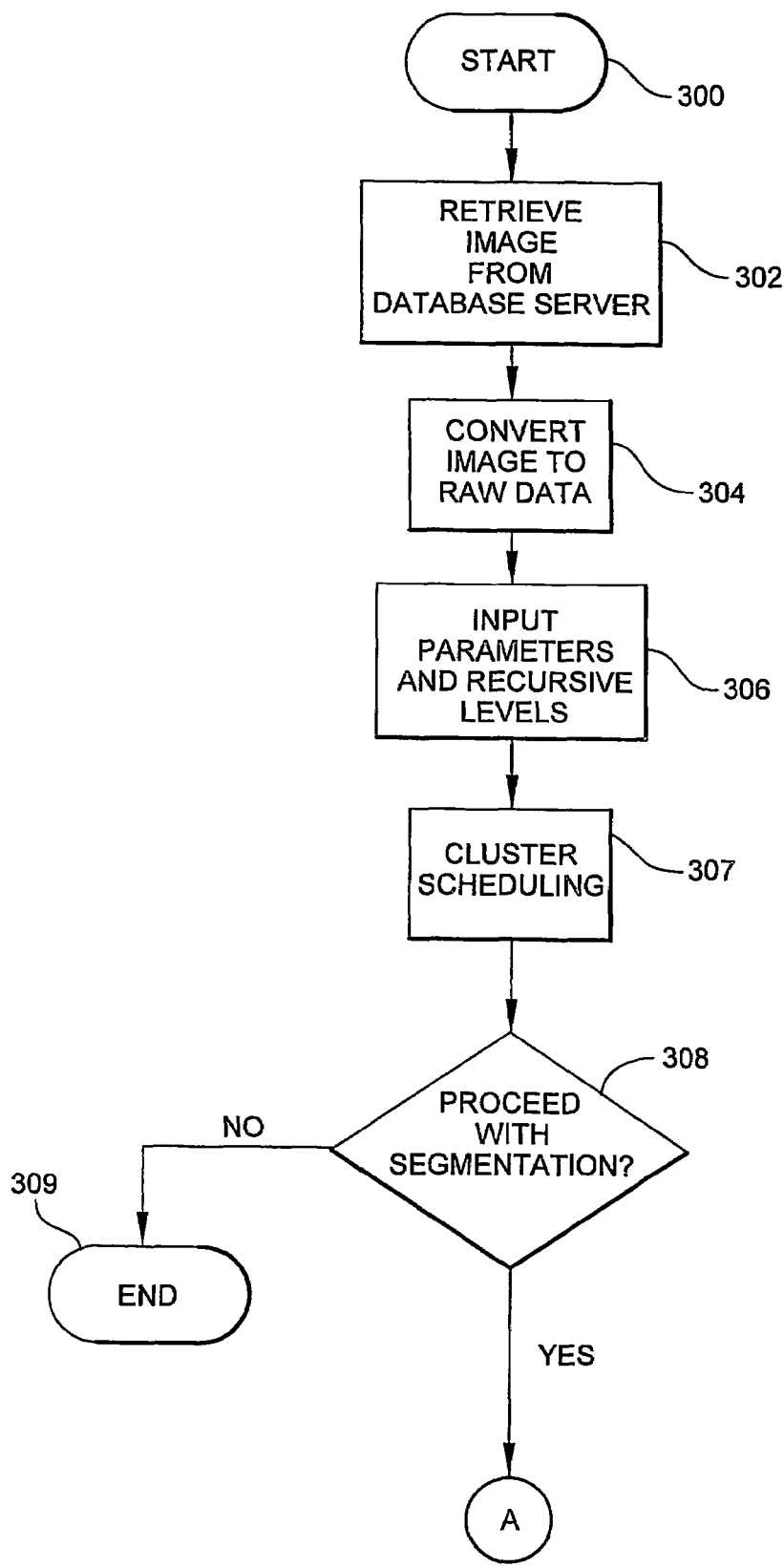

Referring to FIG. 1, in one embodiment of the invention, image management diagnostic subsystem 100b is centrally located. In a preferred embodiment, subsystem 100b is configured to serve a plurality of subsystems 100a and provide diagnosis information in near real time. Subsystem 100b generally comprises communications module 180, antenna 181, temporary image memory 182 and image processing system 190. Communications module 180 receives the digitized image data transmitted by communications module 110 of subsystem 100a. In one embodiment, communications module 180 is realized by the commercially available DSL Speedstream Model 5260 described in the foregoing description. This received digitized image data is then transferred to temporary image memory 182. The stored digitized image is then transferred from temporary image memory 182 to image processing system 190. Referring to FIG. 5, there is shown a block diagram of image processing subsystem 190. Image processing system 190 comprises work stations 200, 202 and 204 which are in electronic data communication with common hub 206. In one embodiment, work stations 200, 202 and 204 are commercially available Pentium™ class computers which are manufactured by Linux™, Sun™, and Microsoft™, respectively. In one embodiment, common hub 206 is configured as a commercially available switch such as a Hewlett Packard or compatible 10/100/1000 hub. Image processing system 190 further comprises master node 208 and firewall 210 between master node 208 and common hub 206. Master node 208 comprises data processing modules that effect implementation and execution of the particular image processing and analysis computer programs that are described in the ensuing description. In a preferred embodiment, master node 208 is configured to implement high-speed parallel processing. In one embodiment, master node 208 comprises a Scyld Beowulf Computer Cluster which has a parallel processor comprising 64 nodes. The Scyld Beowulf Computer Cluster is known in the art and was developed by the NASA Goddard Space Flight Center. Image processing subsystem 190 further comprises central hub 212. In one embodiment, central hub 212 is configured as a commercially available switch such as a Hewlett Packard or compatible 10/100/1000 hub. Image processing subsystem 190 further comprises a plurality of slave nodes 214 that are in electronic data communication with central hub 212. In one embodiment, there are sixty-four slave nodes 214 and each slave node 214 is configured as a PC Pentium class computer having a minimum of 128 MB of RAM. Image processing system 190 further comprises database server 220. Database server 220 stores the image data that originated from subsystem 100a (see FIG. 1) and which is to be analyzed by subsystem 100b. Data base servers are known in the art and need not be discussed herein in detail. Image processing system 190 further comprises file server image repository 222 which has sufficient data storage capacity. Repository 222 has first and second sections. The first section is for storing images of known pathogens, bacteria and abnormal cells. Specifically, the first section contains a large library of reference images of pathogens, abnormal cell structures, bacteria, etc. with several different views of each type to account for rotation and other apparent differences. Preferably, the referenced images are compressed to minimize the memory requirements. Each reference image has corresponding identification information that provides information about the reference image such as the name of the pathogen, bacteria, cell, etc. The second section of repository 222 is for the storage of segments of images produced by a hierarchical segmentation process that is described in the ensuing description.

Referring to FIGS. 1 and 5, images outputted by temporary image memory 182 are inputted into database server 220. Images in database server 220 are routed to master node 208 by using any of the workstations 200, 202 and 204. Master node 208 performs several functions. Master node 208 performs a pre-scan of the digitized images received from database server 220 to determine if the digitized images contain relevant and useful information. If the images do not contain relevant and useful information, the images are either discarded (i.e. deleted) or stored in a designated area in file server image repository 222. If the images do contain relevant and useful information, the images are then subjected to further processing. Specifically, master node 208 performs segmentation on the image. In one embodiment, master node 208 is programmed to execute a segmentation process described in pending U.S. patent application Ser. No. 09/839,147 entitled "Method For Implementation Of Recursive Hierarchical Segmentation On Parallel Computers", the disclosure of which is incorporated herein by reference. The aforementioned pending U.S. application Ser. No. 09/839,147 was published on May 1, 2003 having Patent Application Publication No. US 2003/0081833. Publication No. US 2003/0081833 is incorporated herein by reference. The segmentation process isolates particular features of the digitized image. Specifically, this segmentation process effects a sequential set of image segmentations at different levels of segmentation detail in which the segmentations at a relatively coarser level of detail is produced from simple mergers of regions from segmentations of finer levels of detail. A unique feature of the hierarchical image segmentation process is that the segmented region boundaries are maintained at the full image spatial resolution at all levels of segmentation details in the hierarchy. The result of the process is that regions of similar characteristics are isolated (segmented) and identified. Thus, the image of a pathogen that has features distinct from the background and debris can be isolated using certain assigned criteria, e.g. color, shape, size, etc.

Master node 208 then performs a fast analysis on the isolated feature based on a few descriptors such as size and shape of the isolated feature. Master node 208 includes a memory for storing criteria that is used in the fast analysis to determine whether or not a particular image of an isolated feature has useful information. If the particular image has useful information, the particular image is retained and made available for further analysis. If it is determined that the particular image does not have useful information, the particular image is discarded. If a particular image of an isolated feature does have useful information, master node 208 performs further processing on that image. Specifically, master node 208 implements and executes a computer program that effects optical recognition and data mining. In one embodiment, this computer program is configured as the computer program referred to as "Continuously Scalable Template Matching" developed by NASA Jet Propulsion Laboratories and CalTech. This computer program comprises a first portion that effects data mining and a second portion that effects optical recognition. The data mining portion is configured as the computer program known as "Diamond Eye" which is known in the art and developed by NASA's Jet Propulsion Laboratory. The "Diamond Eye" computer program is based on a distributed applet/server architecture that provides platform-independent access to image mining services. A database associated with "Diamond Eye" computer program provides persistent storage and enables querying of the "mined" information. The computational engine carries out parallel execution of the most demanding parts of the data-mining task: image processing, object recognition, and querying-by-content operations. The purpose of the data mining process is to extract desired, particular image data from the isolated feature or features of the subject image that result from the segmentation process described in the foregoing description. The user inputs particular data that defines the parameters of the image data that is to be mined from the isolated feature or features of the subject image.

The optical recognition portion of the computer program executed by master node 208 comprises a pattern recognition program that determines whether the mined data obtained by the data mining portion of the computer program matches or corresponds to any reference images in the reference library portion of file server image repository 222. The optical recognition program can detect patterns that differ in size but are otherwise similar to a specified (reference) pattern. If a match or correspondence exists, the reference image, the subject isolated feature which matches or corresponds to the reference image, and any information associated with the reference image, are displayed on the displays of work stations 200, 202 and 204. Master node 208 also effects execution and implementation of an image analysis program that performs statistical analysis on the subject isolated feature to identify areas of interest which aids medical personnel in making a diagnosis. One suitable image analysis program is the ImageJ program developed at the National Institute of Health. As a result, medical personnel can make a diagnosis upon viewing the resulting information at any of work stations 200, 202 and 204. If there is no matching or corresponding reference image for a subject isolated feature, then such information is displayed at work stations 200, 202 and 204.

Master node 208 also implements and executes a scheduling program, described in detail in the ensuing description, which effects cost and time efficient scheduling of all of the nodes of image processing system 190. Thus, whether there are 16, 64 or 128 nodes in image processing system 190, the nodes will be used efficiently to achieve optimum operation in a cost efficient manner.

Referring to FIGS. 5A-5D, there is shown a flow chart of the image processing method implemented by image processing system 190. The method starts in step 300 upon a command inputted by a user into any of work stations 200, 202 and 204. In step 302, a user uses any of the work stations 200, 202 and 204 to retrieve an image from database server 220. The image retrieved is the image that is to be processed and analyzed by master node 208. As described in the foregoing description, the retrieved image can be in JPEG, TIFF or other format. In step 304, master node 208 converts the retrieved image into raw data that is suitable for processing by master node 208. In step 306, the user may input commands into work stations 200, 202 and 204 such as parameter data and recursive level data for use by the hierarchical segmentation process implemented by master node 208. The parameter data includes the number of regions in which the subject image is to be divided. Each region defines a specific portion of the image in which medical personnel are interested in analyzing. The recursive level data defines the desired bit resolution and the bandwidth required to process the images. In an alternate embodiment, the parameter data and recursive level data are not inputted by the users but rather, are preset within the software. Next, step 307 effects implementation of a cluster scheduling program that schedules use of the clusters within master node 208 in order achieve time and cost efficient operation and use of the clusters. Thus, step 307 ensures that all clusters are always performing tasks at any given moment and that no clusters are idle. Step 307 also schedules time and efficient operation and use of file server image repository 222 and database server 220. The scheduling program is described in the ensuing description. Next, in step 308, it is determined if the method is to proceed with the hierarchical segmentation process. If the method is not to proceed with hierarchical segmentation, then the method ends at step 309. If the method is to proceed with hierarchical segmentation, the method proceeds to steps 310, 312 or 314. Step 310 determines whether the retrieved image shall be formatted into RGB (Red, Green, Blue) format prior to the retrieved image being segmented by hierarchical segmentation. If RGB format is desired, the method shifts to step 318 wherein the hierarchical segmentation process begins. If RGB format is not desired, the method shifts to step 312. In step 312, it is determined whether the retrieved image shall be formatted into eight (8) bit format prior to the retrieved image being segmented by hierarchical segmentation. If eight (8) bit is desired, the method shifts to step 318 wherein the hierarchical segmentation process begins. If eight (8) bit format is not desired, the method shifts to step 314. In step 314, it is determined whether the retrieved image shall be formatted into sixteen (16) bit format prior to the retrieved image being segmented by hierarchical segmentation. If sixteen (16) bit format is not desired, then the method shifts to step 315 which resets the parameters. The method then shifts to step 316 which causes the method to return to the beginning, step 300. If sixteen (16) bit format is desired, the method shifts to step 318 wherein the hierarchical segmentation process begins. As is apparent from the foregoing description, the decision process performed by steps 310, 312 and 314 depends upon the recursive levels inputted in step 306. In step 318, the hierarchical segmentation process begins and breaks the retrieved image into segments. Each segment defines a particular region of the retrieved image (retrieved in step 302). In step 320, it is determined whether the segments are to undergo further processing or whether the segments are to be stored in repository 222. If step 320 determines that the segments of the particular regions are not to undergo further processing, then step 322 effects storage of these images of the particular regions in repository 222. If step 320 determines that the segments are to undergo further processing, then the method shifts to step 324 wherein the regions defined by the segments are mapped. Specifically, step 324 effects mapping or assignment of labels to each region. In step 325, the labeled regions are stored in repository 222.

Next, in step 326, the users input data defining desired CSTM (Continuously Scalable Template Matching) models into master node 208 via any of the work stations 200, 202 and 204. Specifically, this data defines the desired models that are to be created based on the reference images stored in image repository 222. These models are based on specific features and characteristics of certain pathogens, bacteria or other disease. Next, step 327 then determines if the CSTM models exist in the labeled regions stored in repository 222. This step is accomplished by execution of the "Continuously Scalable Template Matching" program described in the foregoing description. If the CSTM models do not exist in the labeled regions stored in repository 222, then the method shifts to step 328 which sends data to work stations 200, 202 and 204 that indicates that no match has been found. If step 327 determines that there are CSTM models that match or correspond to labeled regions stored in repository 222, then the method shifts to step 330 which effects retrieval of the labeled images defining the particular region or regions to which the CSTM model or models correspond. In step 332, the retrieved labeled images are displayed at work stations 200, 202 and 204 so as to enable medical personal to review the retrieved image and make a diagnosis. The method then ends at step 334.

Figure 6:
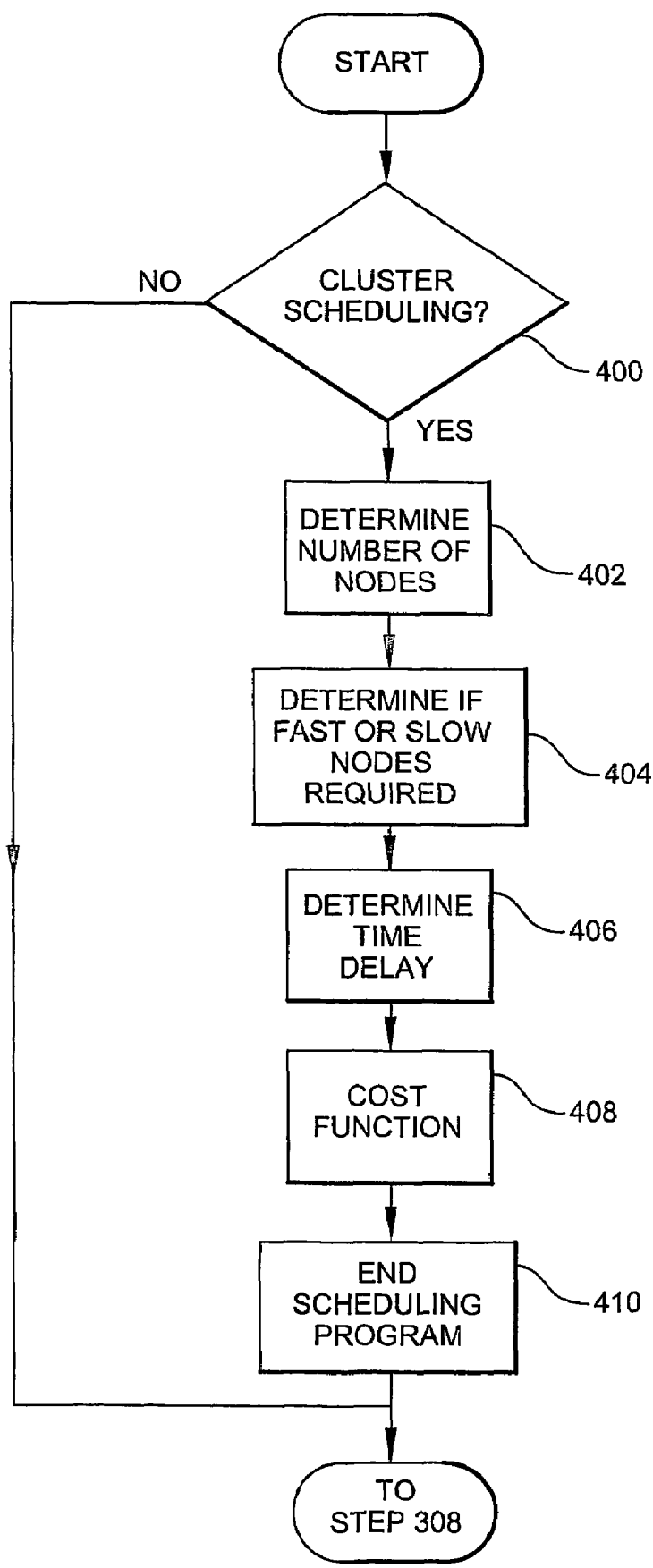
FIG. 6 is a flow chart illustrating a cluster scheduling process used by the image management diagnostic subsystem shown in FIG. 5.

Referring to FIG. 6, there is shown a flow chart of the cluster scheduling program of step 307. In step 400, it is determined whether the cluster scheduling program is to be executed. If the cluster scheduling program is not to be initiated, the cluster scheduling program is terminated and the method implemented by master node 208 shifts to step 308 (see FIG. 5A). If the cluster scheduling program is to be executed, then the program shifts to step 402. Step 402 determines the number of nodes that are being requested to process the subject images. Thus, step 402 determines if four (4), sixteen (16), sixty four (64), one hundred twenty (128) or more nodes are requested. In step 404, it is determined if fast nodes or slow nodes are being requested for processing the subject retrieved images. Whether fast or slow nodes are used depends upon the amount of images to be processed and the time factors dictated by any particular situation, e.g. emergency, chemical warfare scenario, etc. In step 406, it is determined whether there will be a time delay associated with any of the required nodes. Specifically, step 406 determines if there will be a time delay before particular nodes are available for processing the subject retrieved image. The time delay is the amount of time needed by that node to complete its other task. Thus, if a particular node is busy on another task, master node 208 will schedule that node to be used for processing the subject retrieved image upon expiration of the amount of time needed by that node to complete its other task. Similarly, master node 208 schedules nodes to commence new tasks upon completion of the current tasks. Whether there will be time delays depends upon many factors such as the recursive levels, the desired number of nodes, and whether fast or slow nodes are required. Next, step 408 calculates the cost factor for this particular processing task. The cost function depends upon the recursive levels, the desired number of nodes, whether the fast or slow nodes are required, and any time delays. Thus, the cost factor can be varied if any of these preceding factors are varied. The cost factor information is displayed on any of work stations 200, 202 and 204. Mathematical algorithms known in the art are used in determining the cost factor. In step 410, the cluster scheduling program terminates and the overall process implemented by master node 208 resumes at step 308.

The particular hierarchical segmentation and template matching computer programs and algorithms described in the foregoing description are examples of suitable programs and algorithms that facilitate realization and working of the invention. Thus, it is to be understood that other suitable segmentation and template matching programs may also be used as well.

The present invention provides many advantages and benefits, such as:

a) elimination of the need for cultures;

b) provides for rapid and accurate identification of pathogens, bacteria, infectious diseases and abnormal cells;

c) allows separation of the image acquisition subsystem from the image processing and identification subsystem to allow remote operation under demanding conditions;

d) uses multiple data transmission paths to take advantage of the available communication systems;

e) uses a relatively low-cost parallel processing computer system to achieve near real-time operation;

f) combats infectious diseases, reduces morbidity and mortality, and provides high-level medicine to remote areas of the nation and the world;

g) effects diagnosis of infectious diseases due to bacteria, and detection of bacterial contamination of foodstuffs;

h) subsystem 100a can be located in small hospitals and clinics, particularly in rural or remote areas such as Appalachia and Indian Reservations, as well as in Third World countries with limited access to healthcare facilities;

i) subsystem 100a can be located in large slaughterhouses, meat and poultry processing facilities, large dairy farms and other agribusinesses in order to enable detection of bacteria before such meat, poultry and dairy products are shipped to consumers; and j) subsystem 100*a* can be located at research laboratories, the Center for Disease Control, and pharmaceutical manufacturers to aid in research and in the development of new antibiotics.

Although the foregoing description is in terms of the present invention being directed to the rapid identification of pathogens, bacteria and abnormal cells, the system and method of the present invention can be used as a diagnostic radiology and imaging tool in the medical and dental field. Specifically, the system and method of the present invention can be configured to analyze medical images such as images of soft tissue, mammograms, x-rays (bone and dental), ultrasounds, MRI images, and CAT scans. In such an embodiment, the aforementioned images are segmented to generate regions for identification in generally the same manner as the digital microscope images described in the foregoing description. Specifically, the image is transferred to image processing system 190 wherein workstations 200, 202, and 204 are used to compress the images. In a preferred embodiment, loss-less compression software programs, known in the art, are used. Preferably, the compression software is certified for use on medical images. Suitable compression software is GZIP and BZIT2. Other suitable compression software can be used. Next, the compressed image is stored into file server image repository 222. The compressed image is stored in repository 222 and is subsequently retrieved so it can be segmented and/or compared against another image, segment or region. After the compressed image is retrieved from repository 222, the compressed image is prepared for segmentation using the recursive hierarchical segmentation program described in the foregoing description. Preferably, the aforementioned recursive hierarchical segmentation program is performed on a parallel computing platform as described in the foregoing description (e.g. master node 208). As described previously herein, the image segmentation process comprises partitioning an image into sections or regions. These regions may be subsequently associated with normal, abnormal or deviations in various tissues, however, the segmentation process simply gives generic labels to each region. The regions consist of groups of multi-spectral or hyper-spectral image pixels that have similar data feature values. These data feature values may be the multi-spectral or hyper-spectral data values themselves and/or may be derivative features such as band ratios or textural features. Simultaneously, regional images that have been segmented into their sections or regions and masked segmented images that have been labeled are stored in repository 220. The images stored in repository 220 can be recalled by the scalable template matching program, described in the foregoing description, for either viewing or matching known or defined segmented regions that have been associated with normal, abnormal or deviations in the radiological images.

The principles, preferred embodiments and modes of operation of the present invention have been described in the foregoing specification. The invention which is intended to be protected herein should not, however, be construed as limited to the particular forms disclosed, as these are to be regarded as illustrative rather than restrictive. Variations in changes may be made by those skilled in the art without departing from the spirit of the invention. Accordingly, the foregoing detailed description should be considered exemplary in nature and not limited to the scope and spirit of the invention as set forth in the attached claims.

What is claimed is:

1. A method for processing an image of a specimen or dental x-ray to identify a pathogen within the specimen or dental x-ray, comprising the steps of:
   providing an image of a specimen or dental x-ray;
   providing a parallel processing computing platform;
   implementing a recursive hierarchical segmentation algorithm on the parallel processing computing platform and processing the image with the recursive hierarchical segmentation algorithm to isolate at least one segment of the provided image that has a feature that is of interest;
   processing the isolated segment with a data mining algorithm to extract particular image data from the isolated segment; and
   processing the extracted particular image data and at least one reference image with an optical recognition algorithm to determine if the extracted image data matches the at least one reference image.

2. The method according to claim 1 wherein the step of providing the image comprises acquiring the image.

3. The method according to claim 2 wherein the step of acquiring the image comprises processing the acquired image to provide pertinent portions of the acquired image.

4. The method according to claim 2 wherein the step of acquiring the image comprises digitizing the acquired image.

5. The method according to claim 4 wherein the step of acquiring the image further comprises digitally enhancing the digitized image.

6. The method according to claim 5 further comprising storing the digitally enhanced image in a data storage device.

7. The method according to claim 1 further comprising displaying the extracted data and the results of processing the extracted image data and each reference image.

8. The method according to claim 1 further comprising providing a data base having a plurality of reference images stored therein.

9. A system for processing an image of a specimen or dental x-ray to identify a pathogen within the specimen or dental x-ray, comprising:
   a device to provide an image of a specimen or dental x-ray:
   a digitizer to digitize the provided image;
   a first data storage device to store the digitized images;
   a second data storage device having at least one reference image stored therein;
   a parallel processing computing platform configured to implement a recursive hierarchical segmentation algorithm, a data mining algorithm and an optical recognition algorithm;
   a work station computer in data communication with the parallel processing computing platform, the work station computer comprising electronic data communication hardware and software that enables the work station computer to control the parallel processing computing platform to (i) process the digitized image with the recursive hierarchical segmentation algorithm to isolate at least one segment of the digitized image that has a feature that is of interest (ii) process the isolated segment with the data mining algorithm to extract particular image data from the isolated segment, and (iii) process the extracted particular image data and each of the reference images with the optical recognition algorithm to determine if the extracted image data matches any of the reference images; and a display device in data communication with the work station computer to display the extracted image data and the results of processing the extracted image data and the reference image with the optical recognition algorithm.

10. The system according to claim 9 wherein the device comprises a device to acquire the image.

11. The system according to claim 9 wherein the device further comprises an enhancer device to digitally enhance the digitized image.

12. The system according to claim 9 wherein the device comprises a video camera.

* * * * *